(12) United States Patent
Pang

(10) Patent No.: US 8,475,640 B2
(45) Date of Patent: Jul. 2, 2013

(54) METHOD FOR MULTIPLEXED CAPILLARY ELECTROPHORESIS SIGNAL CROSS-TALK CORRECTION

(75) Inventor: Ho-Ming Pang, Ames, IA (US)

(73) Assignee: Advanced Analytical Technologies, Inc., Ames, IA (US)

( * ) Notice: Subject to any disclaimer, the term of this patent is extended or adjusted under 35 U.S.C. 154(b) by 263 days.

(21) Appl. No.: 13/012,446

(22) Filed: Jan. 24, 2011

(65) Prior Publication Data

US 2011/0120869 A1 May 26, 2011

Related U.S. Application Data

(63) Continuation-in-part of application No. 12/426,317, filed on Apr. 20, 2009, now Pat. No. 7,901,557.

(51) Int. Cl.
*G01N 27/447* (2006.01)
(52) U.S. Cl.
USPC .................................................. 204/452
(58) Field of Classification Search
USPC ...... 204/601–605, 451–455; 422/70; 356/344
See application file for complete search history.

(56) References Cited

U.S. PATENT DOCUMENTS

| 5,582,705 | A | 12/1996 | Yeung et al. | |
|---|---|---|---|---|
| 5,682,038 | A | 10/1997 | Hoffman | |
| 6,598,013 | B1 * | 7/2003 | Domnisoru et al. | 702/191 |
| 6,788,414 | B1 | 9/2004 | Yeung et al. | |
| 6,833,062 | B2 | 12/2004 | Kennedy et al. | |
| 6,833,919 | B2 | 12/2004 | Kenseth et al. | |
| 6,969,452 | B2 | 11/2005 | He et al. | |
| 7,118,659 | B2 | 10/2006 | Kurt et al. | |
| 7,497,937 | B2 | 3/2009 | Yeung et al. | |
| 7,901,557 | B2 * | 3/2011 | Pang | 204/452 |
| 2006/0198558 | A1 | 9/2006 | Riley et al. | |

OTHER PUBLICATIONS

Ueno, K., et al., "Simultaneous Monitoring of DNA Fragments Separated by Electrophoresis in a Multiplexed Array of 100 Capillaries", Anal. Chem. 66:1424-1431 (1994).

* cited by examiner

*Primary Examiner* — Alex Noguerola
(74) *Attorney, Agent, or Firm* — McKee, Voorhees & Sease, P.L.C.

(57) ABSTRACT

The present invention provides a simple method to correct cross-talk, after the data have been generated. Adjacent signals are simply subtracted from the original observed signal with a repeating process. The data processing is stopped when a predefined condition is met. By this technique, cross-talk can be reduced from >5% to less than 0.1%. And as an additional advantage, this method provides a way to correct the cross-talk without the need to know which peaks are caused by the adjacent capillary signal.

14 Claims, 7 Drawing Sheets

METHOD FOR MULTIPLEXED CAPILLARY ELECTROPHORESIS SIGNAL CROSS-TALK CORRECTION

CROSS-REFERENCE TO RELATED APPLICATIONS

This application is a Continuation-in-part of co-pending, co-owned, and commonly assigned, application Ser. No. 12/426,317 filed Apr. 20, 2009, herein incorporated by reference in its entirety.

FIELD OF THE INVENTION

This invention relates to a method to correct the cross-talk caused from adjacent capillaries in multiplexed capillary electrophoresis (CE) systems.

BACKGROUND OF THE INVENTION

Capillary electrophoresis (CE) instruments use electric fields to separate molecules within narrow-bore capillaries (typically 20-100 µm internal diameter). By applying electrophoresis in a small diameter fused silica capillary column carrying a buffer solution, the sample size requirement is significantly smaller and the speed of separation and resolution can be increased multiple times compared to the slab gel-electrophoresis method. UV absorption and laser induced fluorescence are routinely used as the detection system for CE separation.

Applicant's assignee is the owner of several earlier U.S. patents related to CE systems, see Kensenth et al., U.S. Pat. No. 6,833,919; Kennedy, U.S. Pat. No. 6,833,062; He, U.S. Pat. No. 6,969,452; Kurt, U.S. Pat. No. 7,118,659; and Yeung, U.S. Pat. No. 7,497,937.

CE techniques are employed in numerous applications, including DNA sequencing, nucleotide quantification, mutation/polymorphism analysis, SDS-protein separation, and carbohydrate analysis. In order to improve sample throughput, multiple capillaries or channels are used to perform separations in parallel. For example, in one system a beam expander and a cylindrical lens are used to distribute laser light into a thin line that intersects the axes of the capillaries to provide laser induced fluorescent detection for a multiplexed CE system (K. Ueno et al., Anal. Chem., 66, 1424 (1994)). U.S. Pat. No. 5,582,705 used a laser as the excitation light source for fluorescence detection for a multiplexed CE system, while U.S. Pat. No. 6,788,414 revealed a method to perform UV absorption detection in a multiplexed CE system.

With all of the capillaries or channels illuminated at the same time, scattering, refraction, or reflection of light from neighboring channels will affect the detected channel. That is, detection in one capillary can be influenced by light absorption or fluorescence in the adjacent capillaries, thus affecting trace analysis. This phenomenon is referred to as cross-talk between adjacent capillaries. Cross-talk in the range of 1% to 10% and even higher can be observed in the previously mentioned inventions. For accurate analysis, cross-talk needs to be eliminated if possible.

There is, therefore, a need to reduce or eliminate the potentially negative cross-talk effects for trace analyte detection using CE. There are several prior art patented techniques to overcome the cross-talk issue. For example, U.S. Pat. No. 5,274,240 used a mechanical stage to translate the capillary bundle to observe one capillary at a time. U.S. Pat. No. 5,324,401 used individual optical fibers to collect emission light from each capillary to eliminate cross-talk. U.S. Pat. No. 5,790,727 used a waveguide to collect the fluorescent signal to reduce cross-talk. Yet another U.S. Pat. No. 7,340,048 taught use of a mask to block the unwanted scattering light to reduce the cross-talk from the adjacent capillaries. Although these various implementations of different optical design in the hardware to reduce the cross-talk are effective, the cost and the complication of the hardware designs are high. There is, therefore, a continuing need to develop less expensive alternate methods of eliminating cross-talk without increasing instrument complexity or cost. This invention has its primary objective fulfilling this need.

SUMMARY OF THE INVENTION

The present invention provides a simple method to correct cross-talk, after the data have been generated. Adjacent signals are simply subtracted from the original observed signal with a repeating process. The data processing is stopped when a predefined condition is met. By this technique, cross-talk can be reduced from >5% to less than 0.1%. And as an additional advantage, this method provides a way to correct the cross-talk without the need to know which peaks are caused by the adjacent capillary signal. The method also provides a means to correct cross-talk from multiple adjacent capillaries.

DETAILED DESCRIPTION OF THE INVENTION

Figure 1:
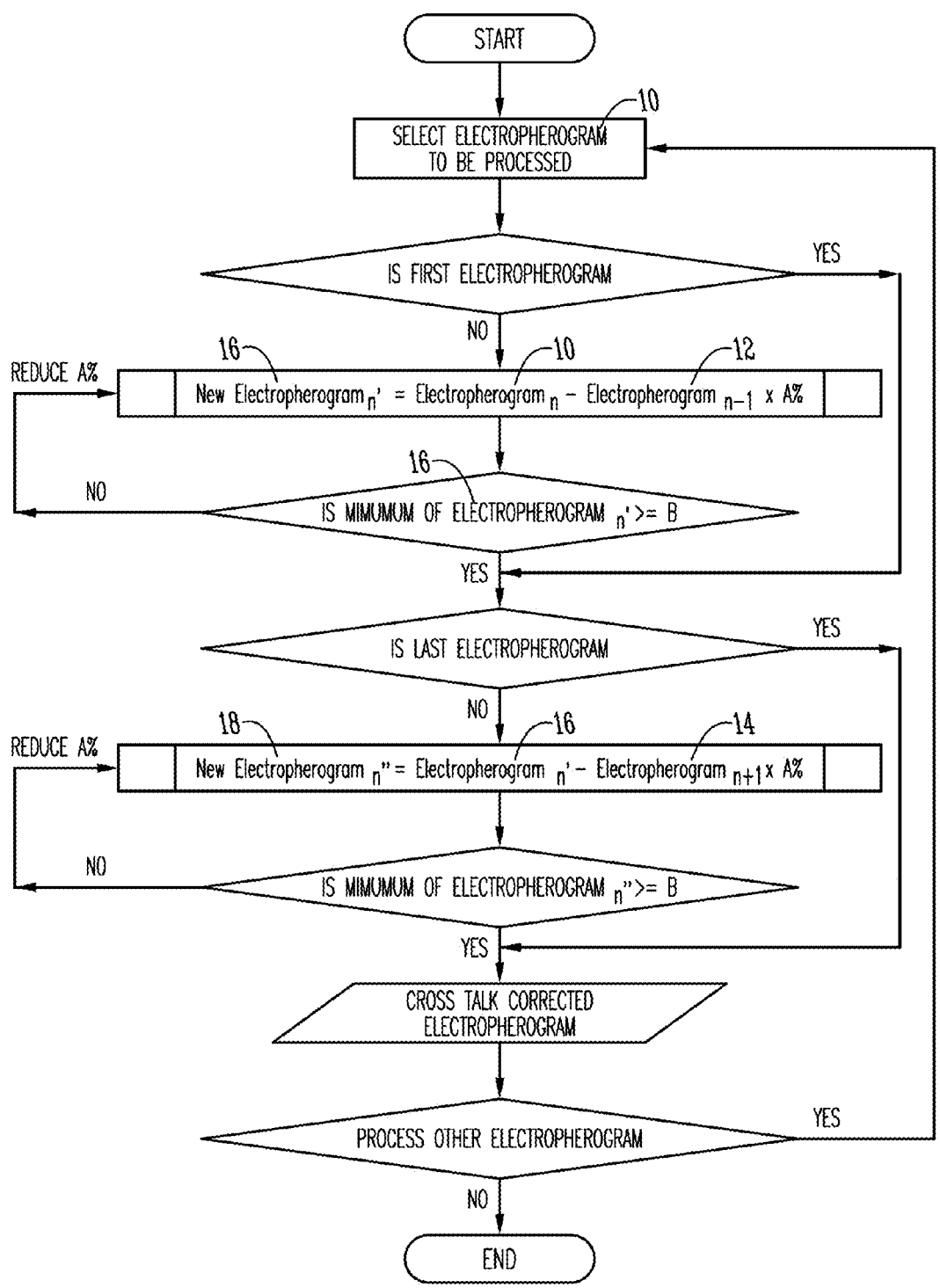
FIG. 1 is a method flow chart to illustrate the process of the present invention.

A specific embodiment of the invention is described in connection with FIG. 1. It is, however, to be understood FIG. 1 is exemplary only. The embodiment is however described in sufficient detail to enable those skilled in the art to practice the invention, and it is to be understood that other embodiments may be utilized and that structural and functional changes may be made without departing from the spirit and scope of the present invention.

The present invention recognizes that cross-talk from the adjacent capillary signal is basically an imposed small percentage of signal of the adjacent capillary into the capillary signal of interest. One could therefore reduce or eliminate the cross-talk by simply subtracting the adjacent capillary signal from the signal of interest, if the corrected percentage of adjacent capillary signal is used. However, in order to know the exact percentage of adjacent capillary signal to subtract out for correction, it is required to know which peaks of an electropherogram are due to cross-talk. One could certainly compare peak by peak in between the electropherogram of interest and adjacent capillary electropherogram to find out which peak(s) is due to cross-talk and then removed it accordingly. However, this process would be time consuming and difficult to implement. The present invention provides an easy approach that requires no prior knowledge of which ones in fact are cross-talk peaks. In the methodology of the present invention, the adjacent signals are simply subtracted from the original observed signal in an iterated process. The data processing is stopped when a predefined condition is met. In this way, cross-talk can be reduced from typically >5% to less than 0.1%, especially when B is a number between −0.1% and −0.5%.

FIG. 1 shows the present invention methodology in flow chart format. The basic process is described in connection with the FIG. 1 flow chart. All electropherograms used in this invention are baseline corrected electropherograms to remove the signal offset or drifting before further data processing. The electropherogram of interest (10) (electropherogram$_n$) is selected to perform the cross-talk reduction. Baseline corrected electropherogram$_{n-1}$ (12), electropherogram$_n$ (10), and electropherogram$_{n+1}$ (14) are the electropherograms from three adjacent capillaries. This baseline correction process sets all electropherogram signal values to $\geq 0$. Electropherogram$_n$ (10) is the center capillary electropherogram of the three adjacent capillaries. Electropherogram$_{n-1}$ (12) and electropherogram$_{n+1}$ (14) are the electropherograms from the capillaries next to the capillary with electropherogram$_n$ (10). One of the adjacent capillary electropherogram (electropherogram$_{n-1}$ (12), or electropherogram$_{n+1}$ (14)) signal is multiplied with a factor (A %) with a value in between 100% and 0%. For example, if the cross-talk signal is no more than 10% of the adjacent electropherogram signal, one could set the factor to be 20%. Or one could use 100% of the adjacent capillary electropherogram signal for subtraction. This resulting smaller electropherogram$_{n-1}$ (12) signal or full scale signal is subtracted from the electropherogram$_n$ (10). The new electropherogram$_{n'}$ (16) value is examined. This modified electropherogram may alternatively be referred to as electropherogram(n)-mod. If there is no negative value, then one could assume that there is no cross-talk from the capillary electropherogram$_{n-1}$ (12). The iteration process is stopped and one then goes to the next step. However, if the electropherogram$_{n'}$ (16) signal has negative value and the valve is smaller than the pre-determined value (B), the previously described process repeats with a reduced A % value until the smallest value of electropherogram$_{n'}$ (16) no longer smaller than the value B. The resulting electropherogram$_{n'}$ (16) will perform another cross-talk correction from another adjacent capillary electropherogram based on the same process described previously to generate cross-talk corrected electropherogram$_{n''}$ (18). In addition, for the first or last capillary electropherogram, only one adjacent capillary electropherogram cross-talk should be corrected.

This same process can be used to correct for cross talk from multiple capillary positions that are located n+1, n+2, n+3 etc. or n−1, n−2, n−3, etc. away from the signal electropherogram (n). That is, cross-talk can be corrected from the immediately adjacent capillary (n+1) or (n−1), as well as capillaries located two positions away (n+2) or (n−2), three positions away, etc. A capillary z positions away is represented as (n+z), which is either a positive or negative integer. If the signal electropherogram(n) is located on the edge of a multiplex array, then adjacent capillaries are located only on one side, that is (n+1), (n+2), etc. If the signal electropherogram (n) is located 1 capillary away from the edge of the array, then one adjacent capillary exists on the edge of the array (n−1), and several adjacent capillaries exist on the other side of the signal electropherogram(n), (n+1), (n+2), etc. To correct for a cross talk from adjacent capillaries, one must first determine if a capillary exists in that position. That is, one must determine if any given capillary position (n+z) exists prior to performing the cross-talk correction iterations.

The extent to which cross-talk is corrected is subjective. If one subtracts out a fraction of the adjacent capillary signal from the signal electropherogram(n), and ends up with negative values, then the cross-talk is over-corrected. However, some degree of over-correction may be acceptable. The extent to which over-correction is acceptable is not critical, and depends on quality criterion set by the user. For example, it may be acceptable to have negative values that are 5% of the adjacent capillary signal. Other units are acceptable for assessing the degree of acceptable over-correction. For example, absolute counts, or negative counts, or a percentage of signal electropherogram could be used as the units for a value expressing the degree of over-correction. As an example, one can use an arbitrary value (B) to represent some acceptable degree of over-correction. If counts from a detector are being used, the value of (B) may be −1000, as an example. If percentages of the maximum signal of an adjacent capillary are used, then the value of (B) may be −0.05%.

In general, the following process can be used for correcting cross-talk induced for any capillary located z positions away from the main capillary position, n:

i. Prepare an observed signal electropherogram(n) for a selected capillary of a multi-capillary electrophoresis system. This preparation process is typically a baseline correction that removes any negative values from the electropherogram, and corrects for baseline shift.

ii. Determine if a capillary exists z capillaries away from said signal electropherogram. This could be 1, 2, 3, or up to 20 capillary positions away. Obviously if a capillary does not exist at position z, no cross-talk correction is required. An example is if a the signal capillary electropherogram(n) is on one edge of the multiplex array. In this case, only capillaries on one side of the signal electropherogram will contribute to cross-talk, namely n+1, n+2, n+3, n+4, n+5, etc. or in general, n+z, where z is any integer from 1 to 20. For the positions n−1, n−2 etc. or in general n−z, these capillary positions do not exist in this particular example, and therefore no cross-talk correction is required for z=−1, −2, etc. up to z=−20.

iii. If the capillary z exists, prepare an observed signal (CE) electropherogram(n+z) for a capillary located z capillaries away from said signal electropherogram(n). Again, this preparation process is typically a baseline correction that removes any negative values from the electropherogram and corrects also for baseline shift.

iv. Select an arbitrary percentage greater than zero and less than or equal to 100% and designate this as A %-value. This value must be less than an arbitrary C value. This C-value selected so that no more than a given amount of adjacent capillary signal (electropherogram(n+z)) can be subtracted out from the signal electropherogram(n). Typically, the starting A % value is the C-value, and each subsequent A % value is reduced. The C-value may be 100%.

v. Multiply the A %-value onto each point of said electropherogram(n+z) to result in a modified signal electropherogram (n+z)-mod.

vi. Subtract said modified signal electropherogram(n+z)-mod from said signal electropherogram(n), resulting in a modified signal electropherogram(n)-mod.

vii. Determine if said modified signal electropherogram (n)-mod has any negative values less than a predefined B value;

viii. If said modified signal electropherogram(n)-mod has negative values than the predefine B value, select a new A %-value, as long as the A % value is smaller than the arbitrary pre-set C value.

ix. Iterate the process steps v)-through viii) until said modified signal electropherogram(n)-mod no longer has any negative values less than the predefined B value.

x. Prepare a corrected multiplexed capillary electrophoresis electropherogram by replacing each value of said signal electropherogram(n) with each corresponding value of electropherogram(n)-mod In one possible process outlined above, one starts with a large A % value and decreases the value until no negative signal is observed in the signal electropherogram(n)-mod.

The A % value during each iteration step can be systematically reduced in such a way as to converge upon a correct value. For example, the A % value can start at the preset C value, and then be reduced in increments of 0.1%, or 0.01% or 0.001% etc. for each iteration until the electropherogram(n)-mod no longer has any negative values less than a predefined B value. Alternatively, the new A % value can be reduced by 50% of the previous A % value for each iteration until no negative values less than predefined B value is reached. However, in this case, an A % value that is too small may be obtained that does not adequately correct for cross-talk correction. An alternative process is to start with an A % value equal to the preset C value, and then reduce each successive A % value by 50% until no negative values are observed in the signal electropherogram(n)-mod or until or until values in electropherogram(n)-mod has values greater than a predefined B value. At this point, increase the A % value by small increments (say 10% of each iterative A % value) until negative values are observed in the signal electropherogram(n)-mod are less than a predefined B value. At this point, decrease the value of A % in even smaller increments (say 1% of each iterative A % value as an example) until no negative values are observed in the signal electropherogram(n)-mod or any negative value in electropherogram(n)-mod has values greater than a predefined B value.

Alternatively the A % value can be increased for each iteration. For example, one can start with a value of 0.01% for the A % value and systematically increase until the electropherogram(n)-mod shows negative values less than a predefined B value. At this point, reduce the A % value systematically until electropherogram(n)-mod shows no negative values or any negative value in electropherogram(n)-mod has values greater than a predefined B value. Alternatively, the A % value can be calculated or predicted based on the percent reduction in cross-talk obtained from the first iteration. For example, if the first iteration reduced the cross-talk by 50%, then doubling the A % value may reduce the cross-talk completely. Any number of predictive calculations or methods to determine the iteration of the A % value may be used. Alternatively, the A % value can be randomly selected between zero and the preset value C.

If one starts with a small A % value, the first iteration of cross-talk correction may not result in any negative values of the electropherogram, in which case larger values of A % can be used for each iteration until one observes a negative value in the signal electropherogram less than a predefined B value. The A % value is then decreased in small increments until the signal electropherogram(n)-mod has no negative values or any negative value in electropherogram(n)-mod has values greater than a predefined B value.

The intent of the invention is to systematically or randomly change the A % value in such a way as to converge upon an optimum value that does not give any negative points in the signal electropherogram or until any negative value in electropherogram(n)-mod has values greater than a predefined B value.

There are an infinite number of iteration strategies that can be used to get the optimum A % value that fully corrects for the cross talk. An example of a generalized process is as follows:

a) Select a value that is greater than zero but less than or equal to 100 and designating this as C % value b) Prepare an observed signal electropherogram(n) for a selected capillary of a multi-capillary electrophoresis system;

c) Determine if a capillary exists z capillaries away from said signal electropherogram, and if so, i. Prepare an observed signal (CE) electropherogram(n+z) for a capillary located z capillaries away from said signal electropherogram(n)

ii. Select a value that is greater than zero or less than or equal to C % value and designating this as A % value iii. Multiply the A %-value onto each point of said electropherogram(n+z) to result in a modified signal electropherogram (n+z)-mod;

iv. Subtract the said modified signal electropherogram (n+z)-mod from said signal electropherogram(n), resulting in a modified signal electropherogram(n)-mod.

v. Select a new A %-value.

vi. Iterate the process steps iii)-through v) until the A % value is equal to said C % value or the A % value is the largest possible value between zero and said C % value without giving any negative values less than a predefined B value.

vii. Replace each value of said signal electropherogram (n) with each corresponding value of electropherogram(n)-mod.

Figure 2:
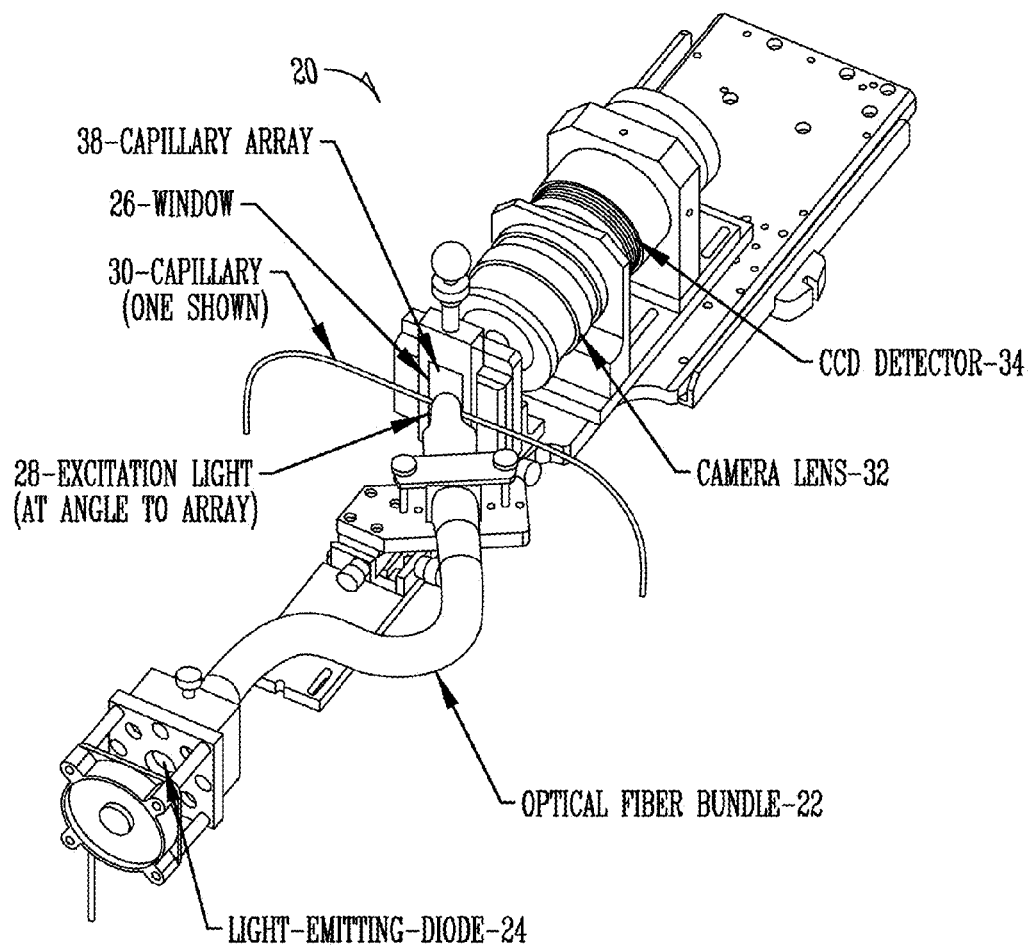
FIG. 2 shows a perspective view of a typical parallel CE system.

FIG. 2 shows the schematic view of a multiplexed CE system with fluorescence detection system that was used to generate the electropherograms of the example. The detailed description of the system setup can be found in our published U.S. patent application Ser. No. 11/299,643, Publication U.S. 2007/0131870 A1, which is incorporated herein by reference. A high throughput detection system referred to generally as 20 is based upon an optical fiber bundle 22 used to deliver a single LED light source 24, instead of an expensive high-powered laser in a multichannel detection system, through a window 26, at preferably an acute angle, the angle being most preferably 45°. The angle of this system is illustrated at 28, the window at 26 and one capillary at 30. An optical camera lens 32 is used for collecting the fluorescent signal and is recorded on a two-dimensional imaging array detector such as a charged couple device (CCD) detector 34. In addition, pixel binning from the detector along the detection window signal is used to improve the signal to noise ratio without losing separation resolution. When imaging the fluorescent signal from the detection windows of the capillary array 38 to the CCD detector 34, each capillary emission signal will cover more than one pixel on the CCD detector 34. The fluorescent light from the detection window irradiates onto multiple pixels of the CCD detector. By combining the corresponding signals together (horizontally and vertically), a higher signal to noise ratio of the detection signal can be obtained.

EXAMPLE

The following example is offered to illustrate but not limit the process of this invention.

Figure 3A:
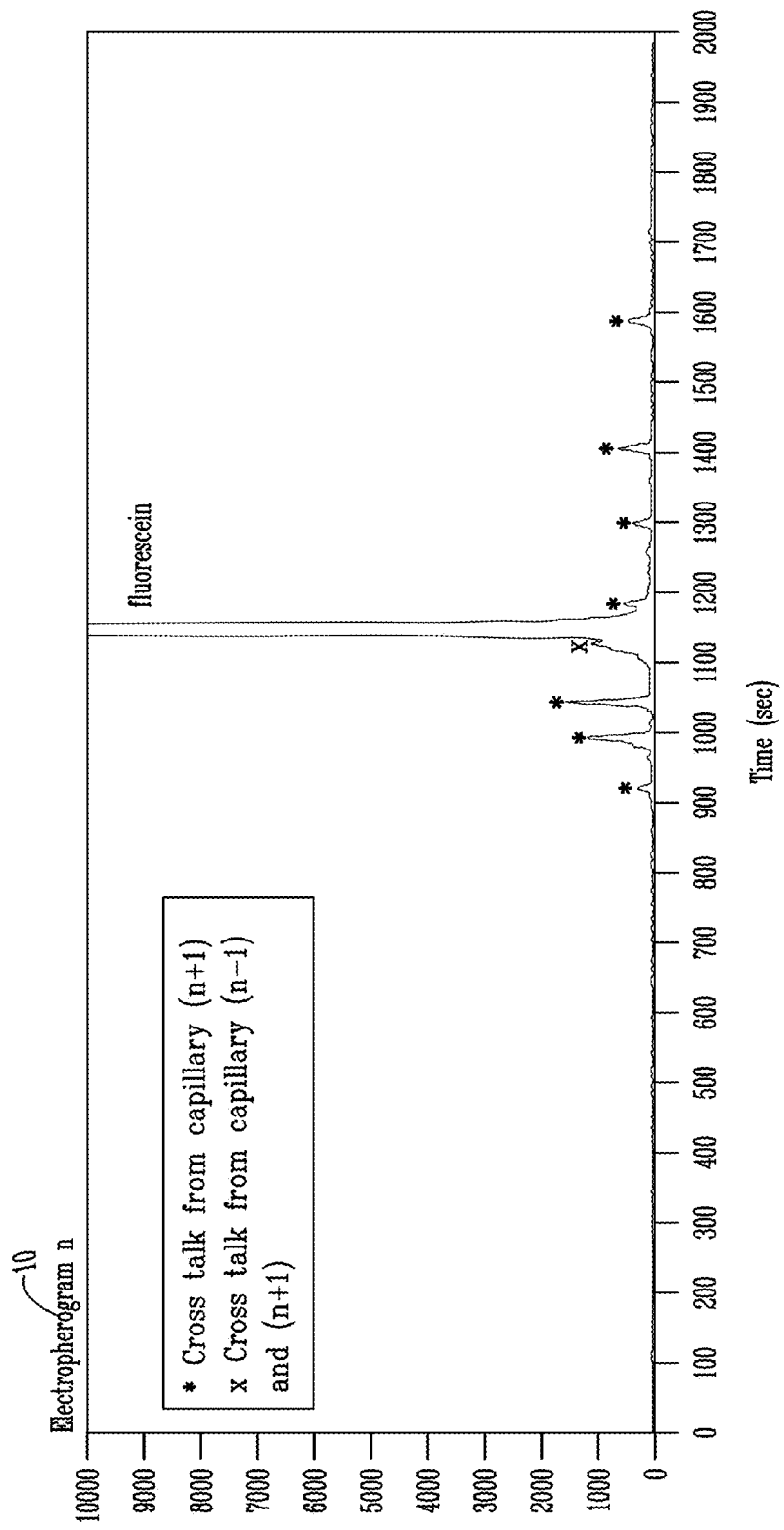
FIGS. 3A, 3B, and 3C show three adjacent capillaries' observed signal electropherograms.
Figure 3B:
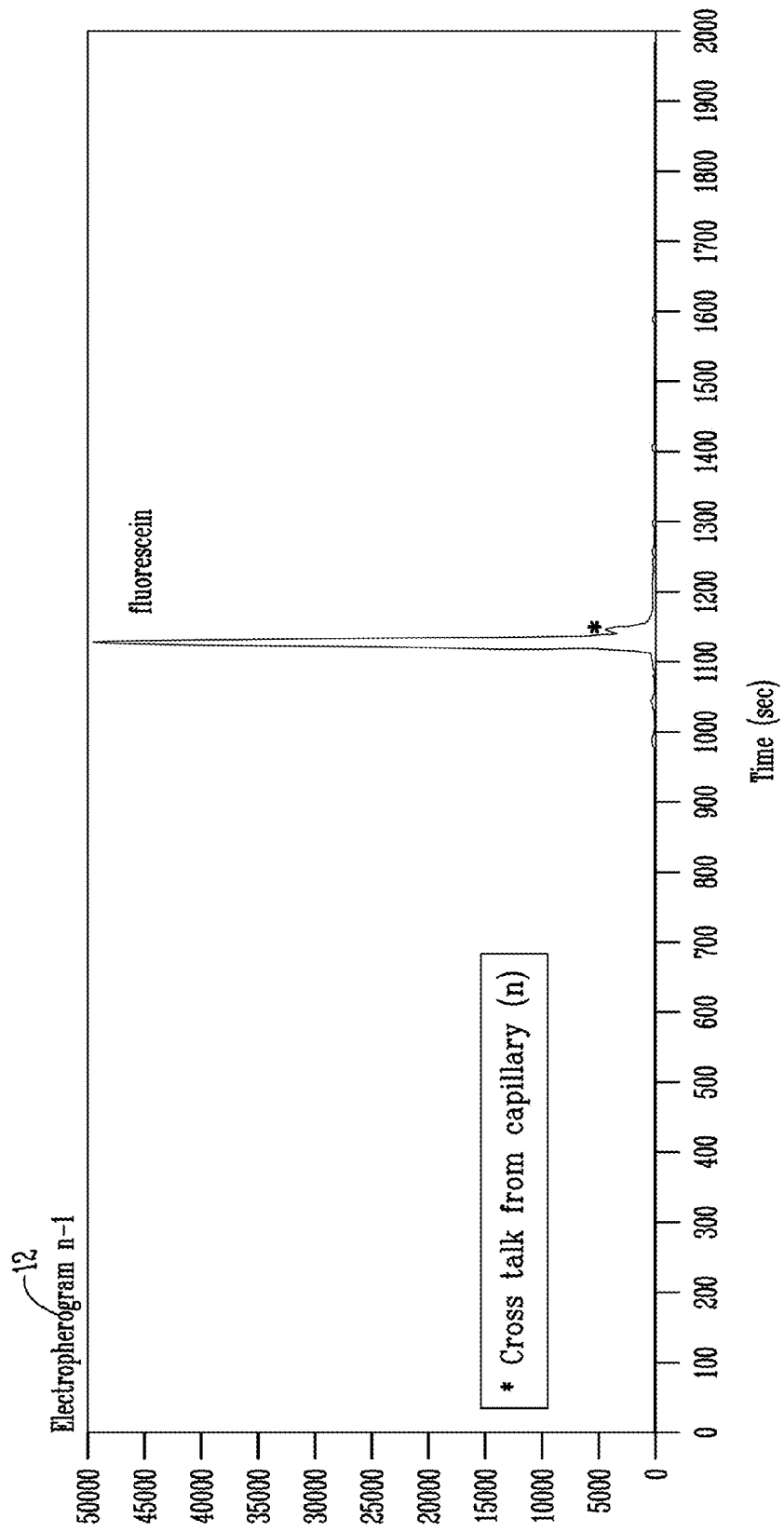
Figure 3C:
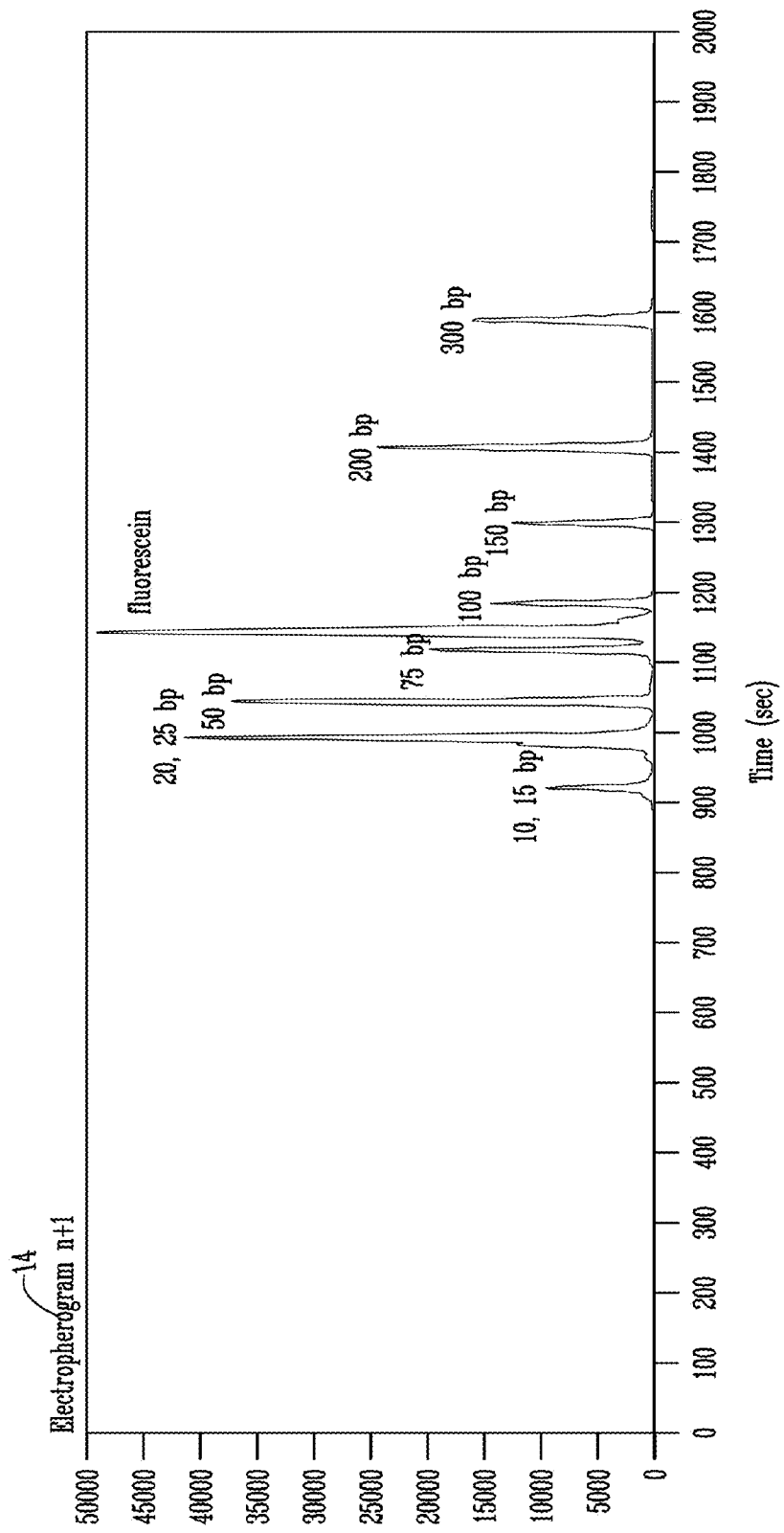

The multiplexed system described in FIG. 2 was utilized to generate electropherograms, FIGS. 3A, 3B and 3C to illustrate the cross-talk correction process. What kind of precise hardware or system (here FIG. 2) that is used to generate the signal is not important, as long as parallel capillaries or channels are used for the simultaneous detection. The capillaries are filled with a sieving matrix that contained a dye such as ethidium bromide that binds to the dsDNA and that fluoresces when excited by the light source. The CCD detector 34 recorded the fluorescence output from the detection windows during the course of electrophoresis separation. Software algorithms were used to extract and re-construct the signal output as electropherograms 3A, 3B, and 3C, i.e., signal intensity change vs. time for each capillary.

FIGS. 3A, 3B, and 3C depict three electropherograms obtained from three adjacent capillaries. For illustrative purposes, capillary n−1 (12) and n (10) were injected with fluorescein dye as sample, while capillary n+1 (14) was injected with DNA ladder and fluorescein mixture as sample. It was obvious for the electropherogram obtained for capillary n (10), significant cross-talk (up to 5%) was observed from both adjacent capillaries (n−1 (12) and n+1 (14)).

Figure 4:
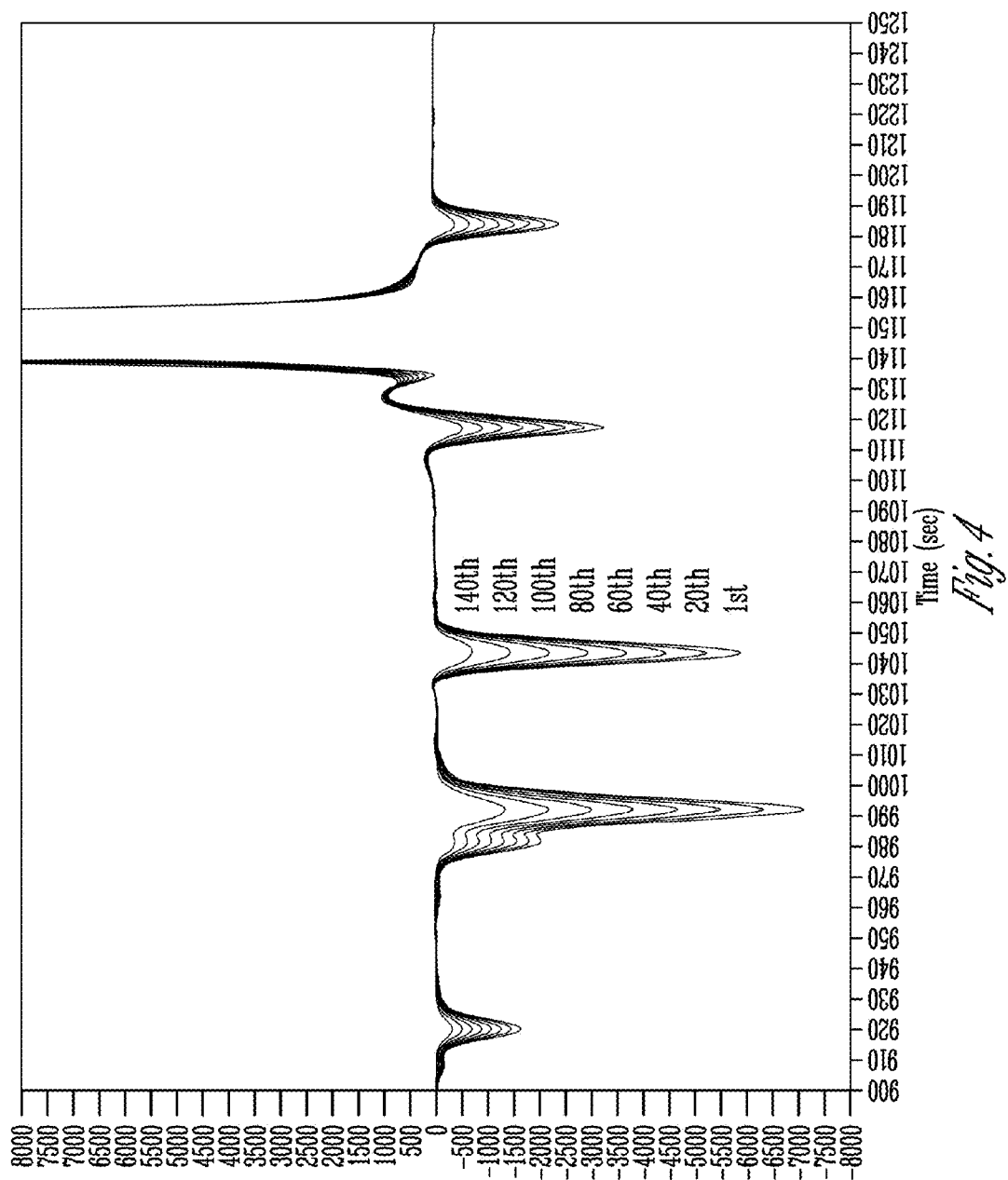
FIG. 4 shows the intermediate step results of the processed electropherogram.

FIG. 4 depicts the intermediate result observed by using the present invention methodology. FIG. 4 shows the process of correcting the cross-talk capillary n electropherogram (10) from capillary n+1 (14) electropherogram. Since in most cases, the cross-talk is less than 10%, one could use 20% of the capillary n+1 (14) electropherogram signal as the starting point for correction. The $1^{st}$ trace shows the first iterate process result of 20% electropherogram$_{n+1}$ (14) signal subtracted from electropherogram$_n$ (10). Because of the over-correction, excess negative peaks are observed. One could reduce the electropherogram$_{n+1}$ (14) signal before the subtraction for the $2^{nd}$ iterate process. For example, the $2^{nd}$ iterate process could then subtracted 19.9% of electropherogram$_{n+1}$ (14) signal from the electropherogram n (10). The $20^{th}$ trace shows the $20^{th}$ iterate process result, while reducing the electropherogram$_{n+1}$ (14) signal to 18.1%. Since the percentage of n+1 (14) electropherogram signal was reduced, a slightly less over-correction was observed here. The $40^{th}$, $60^{th}$, (see FIG. 4) and so on show the corresponding result when the percentage of electropherogram$_{n+1}$ (14) is gradually reduced to 16.1%, 14.1% and so on when each step reduced the electropherogram$_{n+1}$ (14) signal by additional 0.1% for each correction process. The subtraction process is stopped when the minimum value of the subtracted electropherogram is larger than a preset value (B). For example, one could use negative 0.1% of the adjacent capillary's electropherogram maximum value, or an arbitrary value, such as negative 10, as the predefined value to stop the process. Generally, if the selected B value is within the range of −0.10% to −0.50% cross-talk can be reduced from about 4%-5% down to 0.1%.

Figure 5:
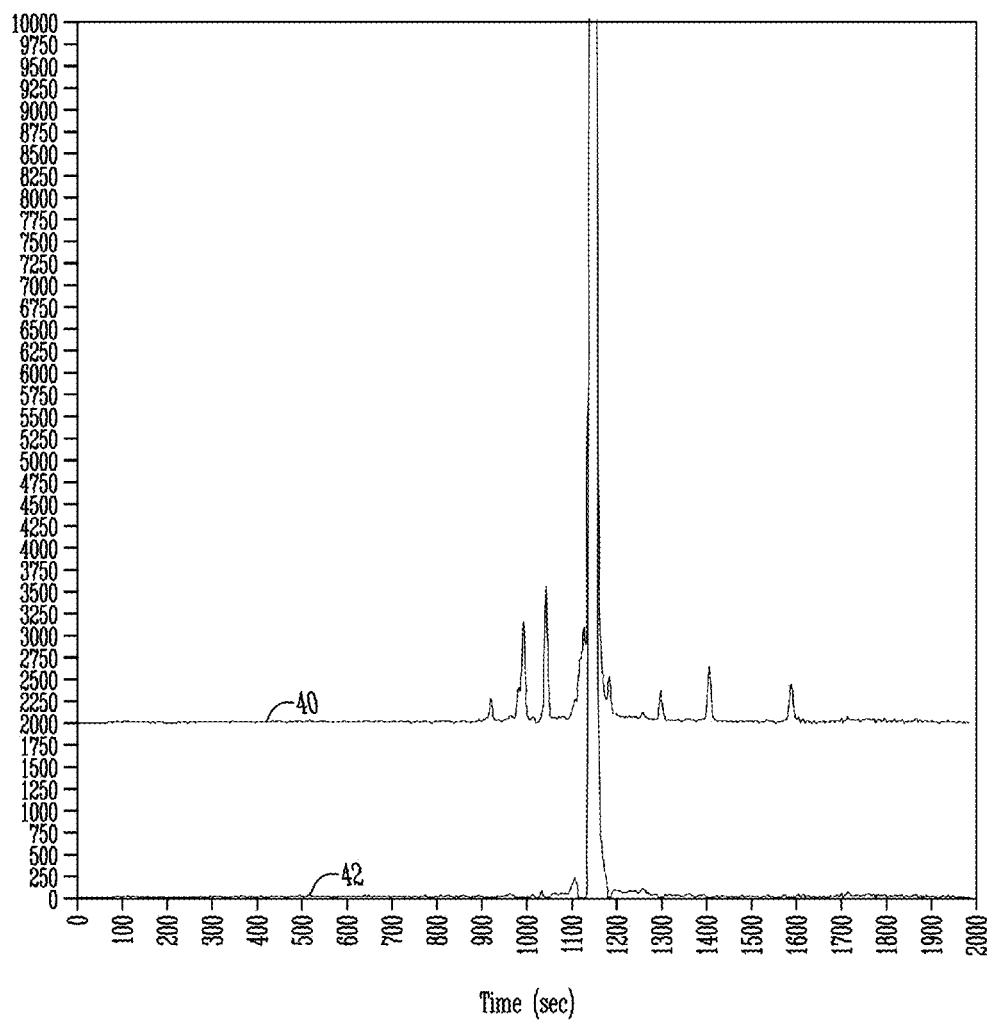
FIG. 5 shows the final result of the cross-talk corrected electropherogram using the present invention vs. original electropherograms of FIG. 3A.

FIG. 5 shows the final result after the cross-talk correction data processing from both adjacent capillaries electropherograms. The upper trace 40 was the original signal while the lower trace 42 showed the processed signal. The upper trace 40 was offset by 2000 count for display purpose. The cross-talk was virtually eliminated. The result indicated that this data processing is effective to reduce/eliminate the cross-talk interference. In FIG. 5, one can easily observe a small impurity signal at about 1110 second on the cross-talk corrected electropherogram (the lower trace 42) while the impurity signal was obscured by the cross-talk signal.

The invention has been shown and described above with the preferred embodiments, and it is understood that many modifications, substitutions, and additions may be made which are within the intended spirit and scope of the invention. From the foregoing, it can be seen that the present invention accomplishes at least all of its stated objectives.

What is claimed is:

1. A method of correcting multiplexed capillary electrophoresis (CE) electropherograms for cross-talk, comprising:
    a) preparing an observed signal electropherogram(n) for a selected capillary of a multi-capillary electrophoresis system;
    b) determining if a capillary exists z capillaries away from said selected capillary, and if so,
        i) preparing an observed signal (CE) electropherogram (n+z) for a capillary located z capillaries away from said selected capillary (n)
        ii) selecting a value that is greater than zero or less than or equal to a preset C % value that is less than or equal to 100 and designating this as A % value
        iii) multiplying the A %-value onto each point of said electropherogram(n+z) to result in a modified signal electropherogram (n+z)-mod;
        iv) subtracting said modified signal electropherogram (n+z)-mod from said signal electropherogram(n), resulting in a modified signal electropherogram(n)-mod;
        v) selecting a new A %-value;
        vi) iterating the process steps III)-through v) until the A % value is the largest possible value between zero and said C % value without giving any values in electropherogram(n)-mod less than a predefined B value
        vii) preparing a corrected multiplexed capillary electrophoresis electropherogram by replacing each value of said signal electropherogram(n) with each corresponding value of electropherogram(n)-mod.

2. The method of claim 1, wherein the said signal electropherogram(n) is corrected for cross-talk for each adjacent capillary located z=1 and z=−1 capillaries away from said selected capillary.

3. The method of claim 1, wherein the said signal electropherogram(n) is corrected for cross-talk for each capillary located z capillaries away, from said selected capillary where z has the values −3, −2, −1, 1, 2, 3.

4. The method of claim 1, wherein the said signal electropherogram(n) is corrected for cross-talk for any capillaries located z capillaries away, from said selected capillary where the integer values of z, excluding zero may be selected from the integer values −10 to +10.

5. The method of claim 1, wherein the preparation of electropherograms includes a baseline correction step resulting in electropherograms with no negative values.

6. The method of claim 1, wherein the A % value is increased or decreased in value upon each iteration step v.

7. The method of claim 1, wherein the A % value in step v is calculated or predicted based on the magnitude of cross-talk correction from the previous iteration.

8. The method of claim 1, wherein the A % value in step v is randomly selected between zero percent and a preset C-value.

9. The method of claim 1 wherein the A %-value is within the range of 0.05% to 99%.

10. The method of claim 1 wherein the said predefined B value is between 0.1% and −99% of the largest signal intensity of adjacent signal electropherogram(n+z).

11. The method of claim 1, wherein the final maximum A % value that does not give any negative values in electropherogram(n)-mod less than a predefined B value is determined to within the nearest 1%.

12. The method of claim 1, wherein the final maximum A % value that does not give any negative values in electropherogram(n)-mod less than a predefined B value in electropherogram(n)-mod is determined to within the nearest 0.1%.

13. The method of claim 1, wherein the final maximum A % value that does not give any negative values in electropherogram(n)-mod less than a predefined B value is determined to within a range of the nearest 1% to the nearest 0.1%.

14. The method of claim 1 wherein the C value is between 1% and 99.9%.

* * * * *

UNITED STATES PATENT AND TRADEMARK OFFICE
CERTIFICATE OF CORRECTION

PATENT NO. : 8,475,640 B2  
APPLICATION NO. : 13/012446  
DATED : July 2, 2013  
INVENTOR(S) : Ho-Ming Pang Page 1 of 1

It is certified that error appears in the above-identified patent and that said Letters Patent is hereby corrected as shown below:

In the Claims:

Col. 8, Claim 10, Line 60:
DELETE after between "0.1%"
ADD after between -- -0.1% --

Signed and Sealed this
Tenth Day of September, 2013

Teresa Stanek Rea
*Acting Director of the United States Patent and Trademark Office*